United States Patent [19]

Gewertz

[11] Patent Number: 4,969,891
[45] Date of Patent: Nov. 13, 1990

[54] REMOVABLE VASCULAR FILTER

[76] Inventor: Bruce L. Gewertz, 5812 Harper Ave., Chicago, Ill. 60637

[21] Appl. No.: 512,029

[22] Filed: Apr. 13, 1990

Related U.S. Application Data

[63] Continuation of Ser. No. 318,957, Mar. 6, 1989, abandoned.

[51] Int. Cl.⁵ ............................................. A61M 29/00
[52] U.S. Cl. ..................................... 606/200; 128/899
[58] Field of Search .................... 606/191, 198, 200; 604/101, 104, 405; 128/899; 210/238, 448, 499; 15/104.011, 104.14, 104.18, 104.33, 242

[56] References Cited

U.S. PATENT DOCUMENTS

| | | | |
|---|---|---|---|
| 1,332,606 | 3/1920 | Chuck | 15/104.011 |
| 3,952,747 | 4/1976 | Kimmell, Jr. | 128/899 |
| 4,425,908 | 1/1984 | Simon | 128/899 |
| 4,494,531 | 1/1985 | Gianturco . | |
| 4,619,246 | 10/1986 | Molgaard-Nielsen et al. | 128/899 |
| 4,688,553 | 8/1987 | Metals . | |
| 4,727,873 | 3/1988 | Mobin-Uddin . | |
| 4,794,928 | 1/1989 | Kletschka | 604/101 |
| 4,832,055 | 5/1989 | Palestrant | 128/899 |
| 4,873,978 | 10/1989 | Ginsburg | 606/200 |

OTHER PUBLICATIONS

Lund et al., Radiology, "A New Vena Caval Filter for Percutaneous Placement and Retrieval: Experimental Study", vol. 152, pp. 369-372 (19-29-84).
Gunther et al., Fortschr, Rontgen, "Animal Experiments with a New Cava Filter", vol. 142, No. 2, pp. 208-212 (1985).
Lund et al., Radiology, "Retrievable Vena Cava Filter Percutaneously Introduced", vol. 155, No. 3, No. 3, p. 831 (1985).
Cook Inc., Advertisement, Gunther Vena Cava Filter Set.
Eichelter & Schenk, Jr. entitled: Prophylaxis of Pulmonary Embolism-Central Surgical Association-Arch Surg-vol. 97, Aug. 1968-pp. 348-356.
Darcy et al. entitled: Short-Term Prophylaxis of a Pulmonary Embolism by Using a Retrievable Vena Cava Filter-Case Report AJR:147, Oct., 1986-pp. 836-838.
Greenfield et al. entitled: A New Intracaval Filter Permitting Continued Flow and Resolution of Emboli-Surgery Apr., 1973 pp. 599-606.
Maass et al. entitled: The Helix Filter: A New Vena Caval Filter for the Prevention of Pulmonary Embolism-J. Cardiovasc. Surg., 26, 1985-pp. 116-123.
Wallace et al. entitled: Inferior Vena Caval Stent Filter AJR:147, Dec., 1986-pp. 1247-1250.
Cragg et al. entitled: A New Percutaneous Vena Cava Filter AJR:141, Sep., 1983-pp. 601-604.
Gunther et al. entitled: Technical Notes-First Clinical Results with a New Caval Filter-Cardiovasc Intervent Radiol (1987) 10:104-108.
Eichelter and Schenk entitled: A New Experimental Approach to Prophylaxis of Pulmonary Embolism-Review of Surgery, 24 pp. 455-456-Nov.-Dec. 1967.

Primary Examiner—C. Fred Rosenbaum
Assistant Examiner—William W. Lewis
Attorney, Agent, or Firm—Garrettson Ellis

[57] ABSTRACT

A vascular filter for capturing blood clots in the vascular system of a patient. The filter is adapted for removable installation through an entry site, and comprises a wire member, plus a filter member permanently attached to one end of the wire member. The filter member comprises a plurality of self supporting filter wires normally diverging outwardly from, and extending forwardly from, the one end of the wire member. The filter wires are capable of being pressed into generally parallel relation with the wire member for installation and removal thereof.

23 Claims, 1 Drawing Sheet

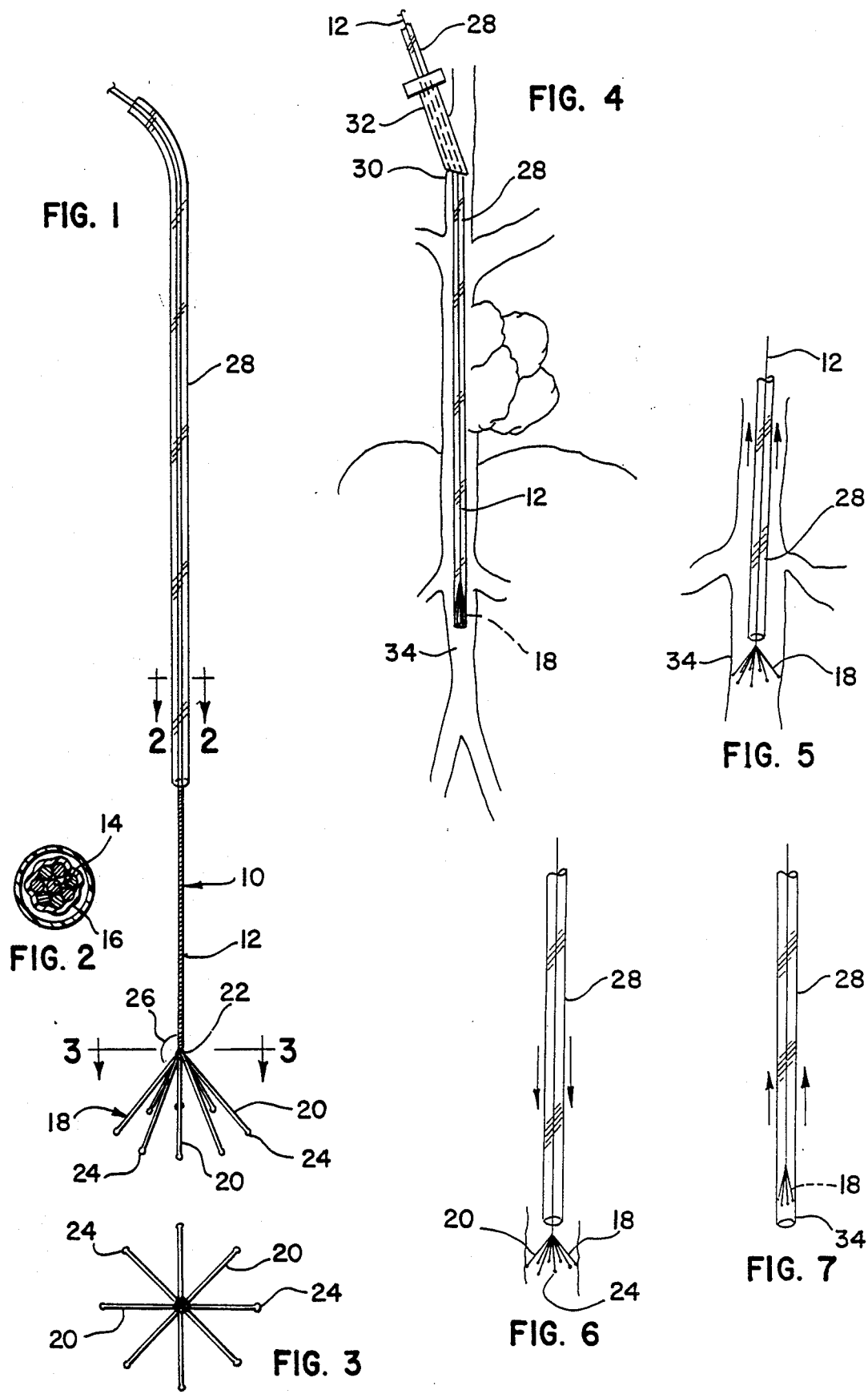

REMOVABLE VASCULAR FILTER

TECHNICAL FIELD

Vascular filters or embolism traps for implantation into the vena cava of a patient are well known, being illustrated, by example, by U.S. Pat. Nos. 4,727,873 and 4,688,553, for example. Additionally, there is a substantial amount of medical literature describing various designs of vascular filters and reporting the results of the clinical and experimented use thereof, see for example the article by Eichelter & Schenk entitled Prophylaxis of Pulmonary Embolism, Archives of Surgery, vol. 97, August 1968, pp. 348 et seq.. See also the article by Greenfield, et al entitled A New Intracaval Filter Permitting Continued Flow and Resolution of Emboli, Surgery, Vol. 73, No. 4, pp. 599–606 (1973).

Vascular filters are used, often during a postoperative period, when there is a perceived risk of a patient encountering a pulmonary embolus resulting from clots generated at the surgical site or the like. As a typical use of vascular filters, the filter is mounted in the vena cava to catch large emboli passing from the surgical site to the lungs.

Typically, the vascular filters of the prior art are permanently implanted in the venous system of the patient, so that even after the need for the filter has abated, the filter remains in place for the lifetime of the patient, unless surgically removed. Peermanent implantation is often deemed medically undesirable, but it has been done because vascular filters are implanted in patients primarily in response to potentially life threatening situations. Accordingly, the disadvantages of permanent implantations of a vascular filter are accepted.

Additionally, while many different configurations of vascular filters are known, many of them require hooks to enter the tissue of the vein wall for proper emplacement. It is, of course, undesirable to cause even minor physical injury to the inner wall of a major blood vessel, but that has been done in the past as part of a trade-off, since it is of course most undesirable for the vascular filter to fall out of position.

In accordance with this invention, a vascular filter is provided which is readily removable from the venous system (or elsewhere) of the patient when it is no longer needed. Additionally, the vascular filter of this invention is of a configuration which does not require hooks to penetrate and grip the blood vessel walls, so that the implantation results in less blood vessel injury.

The filter is inexpensively made, and simple but durable for reliable insertion, filtering, and subsequent removal.

DESCRIPTION OF THE INVENTION

This invention relates to a vascular filter for removable installation in the vascular system of a patient through an entry site, typically the jugular vein. By the improvement of this invention, a wire member is provided, with a filter member permanently attached to one end of the wire member. The filter member comprises a plurality of self-supporting filter wires normally diverging outwardly from and extending forwardly from the one end of the wire member. The filter wires are capable of being pressed into generally parallel relation with the wire member, typically by enclosing the filter member into said generally parallel relation in an introducer sheath which is capable of entering the vascular system of the patient.

Thus, the vascular filter of this invention, in its typical initial condition of use, is provided inside an introducer sheath, positioned adjacent the distal end thereof, with the wire member also occupying the introducer sheath. Then, after the introduction of the distal end of the introducer sheath through an entry site such as an incision or needle puncture through the skin and into the jugular vein, the introducer sheath and vascular filter may be advanced to the desired position, typically in the vena cava. Then, the introducer sheath may be withdrawn while the wire member and the filter member remain stationary, to permit the filter wires of the filter member to expand outwardly toward their normal, unstressed and outwardly and forwardly diverging position, with typically blunt free ends of the filter wires pressing against the wall of the venous site.

The vascular filter is normally positioned so that the blood flow is rearwardly with respect to the outwardly and forwardly diverging filter wires, so that free-flowing blood clots will tend to be caught in a basket-like structure defined by the filter member.

Then, when it is deemed appropriate to remove the vascular filter, one may once again thread the introducer sheath onto the wire member, which wire member typically extends through the entry site, to advance the introducer sheath through the patient's venous system to once again enclose the filter member, forcing the filter wires into generally parallel relation with the wire member. Any remaining clots are entrapped within the introducer sheath as it is thus closed up. Following this, the introducer sheath and introducer filter may be withdrawn out of the entry site.

It is generally preferred for the wire member to be coated with a nonthrombogenic coating. However, the filter wires may be substantially free of nonthrombogenic coating, if desired.

One preferred embodiment of the vascular filter of this invention exhibits a wire member which comprises a secured bundle of wires, each having bent-out distal portions which respectively define the filter wires of the filter member. In this embodiment, the secured bundle of wires may be secured together with a thin sheath of silicone, polytetrafluoroethylene or the like, as a coating or jacket for mechanical securance of the various wires in a typically parallel, spiral or braided array, to define the wire member.

Thus the structure of the vascular filter of this invention is very simple, while its operation is very effective, being firmly positionable a blood vessel to provide clot filtration, and being readily removeable from the patient when that is desired.

DESCRIPTION OF DRAWINGS

In the drawings, FIG. 1 is an elevational view of the vascular filter of this invention, with the filter member shown in its natural, expanded, unstressed configuration.

FIG. 2 is a sectional view taken along line 2—2 of FIG. 1.

FIG. 3 is a sectional view taken along line 3—3 of FIG. 1.

FIG. 4 is a generally schematic view showing the vascular filter of this invention in the process of being installed in the vena cava of a patient for providing clot filtration protection to the patient.

FIG. 5 is a similar, fragmentary, schematic view showing the vascular filter with its introducer sheath being withdrawn allowing extension of the wire members into their outwardly and forwardly extending relation for clot collection.

FIG. 6 is a view similar to FIG. 5, showing the introducer sheath being advanced once again toward the converging filter wires of filter member, for withdrawal thereof from the patient.

FIG. 7 is a view similar to FIG. 6, showing the filter member in its enclosed relation inside of the introducer sheath, for withdrawal of the vascular filter from the venous system of the patient.

DESCRIPTION OF SPECIFIC EMBODIMENT

Referring to the drawings, FIG. 1 shows one embodiment of the vascular filter 10 of this invention, comprising a wire member 12 which, in turn, is made up of a secured bundle of individual wires 14 (FIG. 2) packed together in a thin sleeve 16 which may be preferably made of polytetrafluoroethylene, to hold the individual wires of wire member 12 together. Wires 14 may be in spiral array with respect to each other.

A filter member 18 is provided on the distal end of wire member 12. Filter member 18 comprises in this particular embodiment integral extensions of the individual wires 14, to form a plurality of self-supporting filter wires 20. As shown in FIG. 1, the self-supporting filter wires 20, which are extensions of wires 14, normally diverge outwardly from, and extend forwardly from, the one end 22 of wire member 12. While permanently bent into the configuration shown, filter wires 20 are capable of being pressed into generally parallel relation with wire member 12. It can also be seen that the outer, free ends 24 of filter wires 20 are blunt, typically terminating in a small, rounded member, to limit damage to blood vessel interiors when the filter member 18 is in its operating configuration.

By way of example, wire member 12 and filter member 18 may be about 90 centimeters in length. As shown in FIG. 1, filter member 18 defines a generally conical structure by the diverging filter wires 20, which are typically distinct from the wire member 12 in that they are not surrounded by a sleeve 16, but are generally bare metal, typically stainless steel, along with wires 14. The cone thus defined by filter wires 20 may have a height or altitude of 3 to 5 centimeters, typically 4 centimeters, and a maximum base width of about 3 to 4 centimeters, typically 3.5 cm, to provide a proper fitting into the infrarenal vena cava, as a preferred site for emplacement. It can be seen that variations in the diameter of the vena cava can be readily tolerated, since the filter wire 20 can flex inwardly and outwardly with relative ease to properly fit the vena cava or other major blood vessel. Typically, the filter wires 20 normally define an angle 26 of 120–160 degrees to the axis of wire member 12, when they are freely diverging in unstressed manner as shown in FIG. 1.

Wire member 10 may be threaded through an introducer sheath 28, which may be of a conventional type for penetrating the venous system of a patient to bring the distal end to a desired venous site, for example, the infrarenal vena cava as particularly shown in FIGS. 4 and 5.

Referring to FIGS. 4 and 5, the vascular filter of this invention may be emplaced by providing access through the skin of the patient into the venous system, for example, the jugular vein, at an entry site 30 by means of a conventional hollow needle 32. This provides access to introducer sheath 28, which contains vascular filter 10 with filter member 18 secured within introducer sheath 28 at the distal end 34 thereof. The individual wire members 20 are compressed together in generally parallel relation with wire member 12.

In this manner, filter member 18 and wire member 12 can be advanced along with introducer sheath 28 until the distal end thereof occupies a desired position 34 in the venous system of the patient. It can be seen that the introducer sheath and wire member extend between entry site 30 and position 34 in the venous system, passing in this embodiment through the jugular vein and the atrium, passing the renal veins, to the infrarenal vena cava. Then, when the distal end 34 of introducer sheath 28 is properly positioned as shown in FIG. 4, introducer sheath 28 may be withdrawn while pressing wire member forwardly from its proximal end to prevent its withdrawal. Thus, filter member 18 remains behind with respect to the withdrawing introducer sheath 28.

Filter wires 20 expand outwardly and upwardly, with their free ends entering into engagement with the wall of the vein at the desired venous site 34 for firm retention of filter member 18 in position. Introducer sheath 28 may be completely withdrawn through hollow cannula 32, with the majority of wire member 12 and filter 18 indwelling the venous system. Cannula 32 may also be removed, if desired, so that only wire 12 extends outwardly from entry site 30, with a small, proximal portion being positioned outside of the skin, where it may be taped to the skin during the indwelling period.

Thus, as shown in FIG. 5, filter member 18 serves to protect the lungs or other organs from blood clots that may be generated and may pass through the vena cava, or any other major vein in which the vascular filter is installed.

At the end of the period where use of a vascular filter is indicated, in accordance with this invention, it becomes possible to remove filter member 18 and wire member 12 from the patient. To accomplish this, one reinstalls cannula 32, threading it along wire member 12 to communicate with the jugular vein at entry site 30. One then threads introducer sheath 28 once again along wire member 12, advancing the introducer sheath 28 through cannula 32 as in FIG. 6 until the filter wires 20 of filter member 18 are drawn into the bore of introducer sheath 28 and its distal end 34, as shown in FIG. 7. By this action, the free ends 24 of filter wires 20 are drawn inwardly out of engagement of the wall of the blood vessel, and any clots carried by filter member 18 may be pulled into introducer sheath 28 along with filter member 18.

Then, introducer sheath 28 is withdrawn through cannula 32, followed by removal of the cannula 32 itself, to terminate the procedure.

Accordingly, a vascular filter is provided having the characteristic of being easily replaceable, stable while in place, and easily removeable at termination of its use. The vascular filter is of simple construction, with the wire member and filter wires which comprise the filter member being preferably integral with each other for strength, as well as ease of manufacture.

The above has been offered for illustrative purposes only, and is not intended to limit the scope of the invention of this application, which is as defined in the claims below.

That which is claimed:

1. A vascular filter for removable installation in the vascular system of a patient through an entry site, the improvement comprising, in combination:

a wire member for advancing a filter member in the vascular system, a filter member permanently attached to one end of the wire member, the wire member being at least five times the length of said filter member and sufficiently long to extend out of said patient when the filter member is in its installed position, said wire member comprising a secured bundle of a plurality of wires, a plurality of self-supporting filter wires normally diverging outwardly from, and extending forwardly from, said one end of the wire member, said filter wires being defined by bent end portions of individual wires of said secured bundle, said filter wires being capable of being pressed into generally parallel relation with said wire member.

2. The vascular filter of claim 1 in which said filter member is enclosed in said generally parallel relation in an introducer sheath capable of entering the vascular system of a patient, said wire member also occupying said introducer sheath.

3. The vascular filter of claim 1 in which said wire member is coated with a nonthrombogenic coating.

4. The vascular filter of claim 3 in which said filter wires are substantially free of nonthrombogenic coating.

5. The vascular filter of claim 1 in which said filter wires define free, blunt outer ends.

6. The vascular filter of claim 1 in which said filter member is adapted to be positioned in the venous system of a patient with the filter wires in said outwardly diverging and forwardly extending relation, and said wire member extends through the venous system of the patient to said entry site.

7. The vascular filter of claim 1 in which said filter wires normally diverge outwardly and extend forwardly to provide generally equal spacing to said filter wires about the axis of said wire member.

8. The vascular filter of claim 1 in which said filter wires normally define an angle of 120 to 160 degrees to the axis of said wire member.

9. The vascular filter of claim 1 in which said wire members normally define the shape of a pyramid having a height of about 3 to 5 cm. and a maximum base width of about 3 to 4 cm.

10. The vascular filter of claim 1 in which said self-supporting filter wires in their normally diverging position define a pyramidal shape with the apex thereof pointing toward said wire member.

11. A vascular filter for removable installation in the vascular system of a patient through an entry site, the improvement comprising, in combination:

a wire member for advancing a filter member in the vascular system, said wire member comprising a secured bundle of wires of sufficient length to extend out of said patient when the filter member is in its installed position, said wire member being at least five times the length of said filter member, a filter member permanently attached to one end of said wire member, said filter member comprising a plurality of self-supporting filter wires normally diverging outwardly from, and extending forwardly from, said one end of the wire member, the filter wires comprising integral, bent-end portions of individual wires of said secured bundle of wires, said filter wires being capable of being pressed into generally parallel relation with said wire member.

12. The vascular filter of claim 11 in which said wire member is enclosed in a nonthrombogenic sleeve.

13. The vascular filter of claim 12 in which said filter wires define free, blunt outer ends.

14. The vascular filter of claim 13 in which said filter wires normally diverge outwardly, and extend forwardly, to provide generally equal spacing to said filter wires about the axis of said wire member.

15. The vascular filter of claim 11 in which said filter member is enclosed in said generally parallel relation in an introducer sheath capable of entering the vascular system of a patient, said wire member also occupying said introducer sheath.

16. The vascular filter of claim 11 in which said filter member is adapted to be positioned in the venous system of a patient with the filter wires in said outwardly diverging and forwardly extending relation, and said wire member extends through the venous system of the patient to said entry site.

17. The vascular filter of claim 11 in which said self-supporting filter wires in their normally diverging position define a pyramidal shape with the apex thereof pointing toward said wire member.

18. A vascular filter for removable installation in the vascular system of a patient through an entry site, the improvement comprising, in combination:

a wire member for advancing a filter member in the vascular system, said wire member comprising a secured bundle of wires surrounded by a nonthrombogenic sheath, the wire member being of sufficient length to extend out of said patient when the filter member is in its installed position, a filter member permanently attached to one end of said wire member, said wire member being at least five times the length of said filter member, said filter member comprising a plurality of self-supporting filter wires normally diverging outwardly from, and extending forwardly from, one end of the wire member, said filter wires comprising integral, bent-end portions of the wires of said secured bundle, said filter member being enclosed in an introducer sheath, said filter wires being pressed into generally parallel relation with said wire member within said introducer sheath, said introducer sheath being capable of entering the vascular system of a patient, said wire member also occupying said introducer sheath.

19. The vascular filter of claim 18 in which said filter wires are substantially free of nonthrombogenic coating.

20. The vascular filter of claim 18 in which said filter wires define free, blunt outer ends.

21. The vascular filter of claim 18 in which said filter wires, when separated from said introducer sheath, normally diverge outwardly and extend forwardly to provide generally equal spacing to said filter wires about the axis of said wire member.

22. The vascular filter of claim 18 in which said self-supporting filter wires in their normally diverging position define a pyramidal shape with the apex thereof pointing toward said wire member.

23. The vascular filter of claim 22 in which said wire members have a height of about 3 to 5 cm. and a maximum base width of about 3 to 4 cm.

* * * * *